United States Patent [19]

Hunds et al.

[11] Patent Number: 5,101,031
[45] Date of Patent: Mar. 31, 1992

[54] PREPARATION OF 2,4,5-TRIAMINO-6-HYDROXYPYRIMIDINE BY CATALYTIC HYDROGENATION OF 2,4-DIAMINO-6-HYDROXY-5-NITROSO-PYRIMIDINE

[75] Inventors: Artur Hunds; Walte Rogler, both of Fed. Rep. of Germany

[73] Assignee: Huels Aktiengesellschaft, Marl, Fed. Rep. of Germany

[21] Appl. No.: 662,061

[22] Filed: Feb. 28, 1991

[30] Foreign Application Priority Data

Mar. 2, 1990 [DE] Fed. Rep. of Germany ....... 4006538

[51] Int. Cl.$^5$ ............................................ C07D 239/50
[52] U.S. Cl. .................................................... 544/320
[58] Field of Search ......................................... 544/320

[56] References Cited

U.S. PATENT DOCUMENTS 2,447,523 8/1948 Mozingo et al. .................... 260/251

Primary Examiner—John M. Ford
Attorney, Agent, or Firm—Felfe & Lynch

[57] ABSTRACT

The preparation of 2,4,5-triamino-6-hydroxypyrimidine by catalytic hydrogenation of 2,4-diamino-6-hydroxy-5-nitrosopyrimidine is carried out by performing the hydrogenation in the presence of noble metal catalysts without the addition of basic agents before and during the hydrogenation, and adding the base required for dissolution of the product and for separation of the solution of the product from the catalyst only after the completion of the hydrogenation.

13 Claims, No Drawings

PREPARATION OF 2,4,5-TRIAMINO-6-HYDROXYPYRIMIDINE BY CATALYTIC HYDROGENATION OF 2,4-DIAMINO-6-HYDROXY-5-NITROSO-PYRIMIDINE

FIELD OF THE INVENTION

This invention relates to a novel, improved process for the preparation of 2,4,5-triamino-6-hydroxypyrimidine (TAHP) by catalytic hydrogenation of 2,4-diamino-6-hydroxy-5-nitrosopyrimidine (DAHNP).

BACKGROUND OF THE INVENTION AND THE PRIOR ART

The catalytic hydrogenation of DAHNP is described, for example, in U.S. Pat. No. 2,447,523 and in German Offenlegungsschrift 36 38 635. In accordance with the U.S. patent, a 0.4 to 0.5 molar suspension of DAHNP is hydrogenated at 1.4 to 2.3 bar in 0.1 to 1.0N sodium hydroxide (corresponding to 0.2 to 2.5 mols sodium hydroxide per mol DAHNP) in the presence of palladium, platinum oxide or Raney nickel as a catalyst. This process, however, has several disadvantages. First, the concentration of DAHNP is limited to 0.4 to 0.5 mol/liter, since higher concentrations cause a rapid thickening of the reaction mixture, thus preventing any efficient mixing which in turn greatly slows down the hydrogen uptake. Secondly, the required amount of catalyst is high, reaching 50 g of 5 wt.-% palladized charcoal (corresponding to 2.5 g metallic palladium), 4 g platinum oxide or 150 g Raney nickel per mol DAHNP.

German Offenlegungsschrift 36 38 635 eliminates both of these disadvantages in that DAHNP is hydrogenated under a hydrogen pressure of 1.4 to 21 bar in aqueous solution at 20° to 80° C. and a concentration of 0.5 to 3.0 mol/liter in the presence of 0.02 to 0.2 g metallic palladium (1 to 10 wt.-% on charcoal) per mol of DAHNP while metering in 0.8 to 1.5 mols of sodium hydroxide per mol of DAHNP during the hydrogenation.

Despite these important advantages, the process of the German reference still has the disadvantage that it is, for the most part, performed in the alkaline range. However, with as little as 0.2 mol of alkali per mol of DAHNP, which is the smallest amount of alkali according to the U.S. patent, the pH rises to 12 and, according to the German reference, with ammonia it rises to 10 and more. Attempts to hydrogenate DAHNP in aqueous acid solution failed according to column 1, paragraph 3, of U.S. Pat. No. 2,447,523.

Moreover, we have found that the hydrogenation in the alkaline range has the great disadvantage that significant amounts (up to more than 50%) of the expensive catalytically active noble metals go into solution during the hydrogenation. When the catalyst is then removed by filtration, these noble metals are not recovered and move into the production waste water and into the product TAHP-sulfate from which they cannot be recovered with an acceptable amount of cost and labor. Because of the high price of the noble metals which are used, already small losses negatively affect the economy of the process. Furthermore, the contamination of the TAHP-sulfate, which is further processed into pharmaceutically useful substances, such as guanine and folic acid, is very questionable. Also, the ecological effects of these metals on creeks, rivers and lakes are largely unknown.

OBJECTS OF THE INVENTION

It is an object of the present invention to avoid the loss of noble metals during the catalytic hydrogenation of DAHNP.

Other objects and advantages of the present invention will become apparent as the description thereof proceeds.

DESCRIPTION OF THE INVENTION

We have discovered that the above object is achieved by means of the process of the instant invention in which DAHNP is hydrogenated in an aqueous medium, which may additionally contain organic solvents and/or inert organic salts, in the presence of a noble metal catalyst. The hydrogenation is carried out in an acid, neutral or slightly alkaline range below pH 9. Preferably, no alkaline agents are added before or during the hydrogenation. However, the amount of alkaline agent necessary for dissolving the TAHP is added after the hydrogenation, and the resulting solution is then separated from the catalyst. Preferably, the reaction is carried out in a pH range from 2.5 to 9.0, and especially preferably at pH 3 to 8.5. Thus, the process also includes the hydrogenation under acid conditions. We have found that at elevated temperatures and elevated pressure the hydrogenation proceeds without problems even at pH 2. Such low pH values, however, may be used only if the material of which the hydrogenation apparatus is made is not subject to corrosion.

The process pursuant to the instant invention is performed by admixing a hydrogenation catalyst with an aqueous suspension of DAHNP or with an aqueous DAHNP-suspension obtained during the preparation of DAHNP pursuant to a known process which optionally still contains process salts and/or organic solvents, and reacting the mixture at a pressure of 3 to 150 bar and temperatures of 50° to 150° C. with hydrogen.

In contrast to the previously known processes, the addition of the base required for dissolution of the TAHP during the hydrogenation and separation of this solution from the catalyst is not added until after completion of the reaction. By virtue of this method of operation the dissolution of the noble metals is suppressed.

The concentration of DAHNP may be 0.4 to 3 mols/liter. If isolated DAHNP is used, a concentration of 1.5 to 2.5 mols/liter is preferred, whereas if a salt-containing DAHNP suspension obtained from its preparation is used, a concentration of 0.6 to 1 mol/liter is preferred.

The hydrogen pressure is not critical and in order to achieve higher reaction rates, pressures of 10 to 60 bar are preferred. The preferred temperature range is between 70° and 120° C. At lower temperatures the reaction rate is markedly slower, and at temperatures above 120° C. the resulting products are often dark colored.

Noble metals of Group VIII of the Periodic System such as ruthenium, palladium or platinum in finely divided form, preferably deposited on carrier materials, especially on activated carbon, containing 1 to 10 wt.-%, preferably 4 to 6 wt.-%, palladium or platinum or sufficient amounts of the oxides of these metals, are used as hydrogenation catalysts. Most preferably, 0.2 to 0.02 g of metallic palladium or 0.4 to 0.04 g of metallic platinum per mol of DAHNP is used.

The reaction may be performed in any conventional pressure reactor equipped with stirring or mixing devices. Particularly preferred, however, are propulsion jet loop-type reactors. 0.9 to 1.2 mols of alkali metal hydroxide, preferably 1.1 mols per mol of DAHNP of an aqueous solution of sodium hydroxide or potassium hydroxide are added only upon completion of the reaction in order to dissolve the TAHP. Then, the catalyst is filtered off in known manner, and the oxidation-sensitive TAHP is precipitated in the form of its stable sulfate by letting the filtrate run into aqueous sulfuric acid.

The advantage of the described process resides in the greatly reduced loss of noble metal catalysts. With the high prices of the catalytically active noble metals the economy of the process is greatly improved and a contamination of the product TAHP-sulfate as well as of the production waste water is avoided. This brings another advantage which is that the catalyst, especially after adding a small amount of fresh catalyst, can be used again for subsequent batches, whereby the economy of the process is still further improved. Fresh catalyst can be added to the used catalyst in amounts of 0 to 50%, preferably 5 to 25%.

A further advantage of the process of the present invention resides in that inorganic salts and organic by-products which may be present do not significantly interfere with the reaction. This feature of the process makes it possible that the DAHNP, which is conventionally prepared, for example, from sodium alcoholate, guanidine salt and cyanoacetic acid ester, followed by reaction of the resulting 2,4-diamino-6-hydroxypyrimidine (DAHP) with sodium nitrite and acid pursuant to the following reaction sequence:

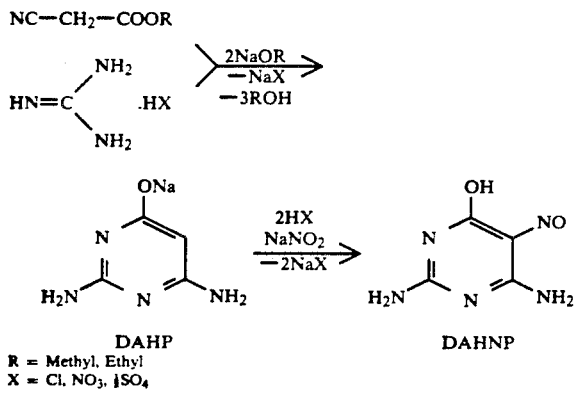

R = Methyl, Ethyl
X = Cl, NO₃, ½SO₄ does not have to be used in isolated form. In accordance with the present invention, the aqueous suspension which is initially obtained in the synthesis of DAHNP and which contains 2.6 to 3.4 mols of sodium salts per mol of DAHNP as well as small amounts of organic by-products, can be used as starting material for the process of the present invention. DAHP or its sodium compound also does not have to be isolated. Since the DAHNP obtained by the conventional processes is very fine and therefore very poorly filterable, the use thereof in the form of a suspension represents a considerable time saving. It is, however, also possible to add alkaline agents for a short time or in small amounts without adversely affecting the invention or the effect on the solubility of the noble catalyst, and then lowering the pH again as long as the noble metal catalyst is not dissolved.

The following Examples illustrate the present invention and will enable others skilled in the art to understand it more completely. It should be understood, however, that the invention is no limited solely to the particular Examples given below.

EXAMPLE 1

In a 2-liter stirrer autoclave, a suspension of 279.2 g (1.8 mols) DAHNP in 650 ml water was adjusted to pH 3.5 by adding a little sulfuric acid, the acid suspension was admixed with 5 g of 5 wt.-% palladized charcoal, the mixture was heated to 60° C., and the autoclave was pressurized with 15 to 20 bar of hydrogen. The temperature was raised to 95° to 100° C., and the mixture was stirred for another 30 minutes. The reaction mixture now had a pH of 5.5 to 6.5 and was only then admixed with 1.98 mols of aqueous sodium hydroxide and thereby adjusted to pH 12. Thereafter, the catalyst was filtered off in known manner, and the filtrate was stirred into 3.15 mols of aqueous sulfuric acid. After suction filtration and washing of the TAHP-sulfate thus obtained, the sulfate and the waste water were tested for palladium by means of atom absorption spectrometry (AAS). Within the detection limit (1 ppm), palladium was not found either in the waste water or in the TAHP-sulfate.

EXAMPLE 2

The catalyst recovered after performance of the reaction described in Example 1, which had a filter-moist weight of about 10 g was combined with 1 g of fresh catalyst and was used again in a further batch as described in Example 1. Here, too, no palladium was found either in the waste water or in the TAHP-sulfate. The catalyst recovered from this mixture could be used again, with 1 g of fresh catalyst being added, for another three batches without any problems. AAS testing did not show any palladium in the waste water or in the TAHP-sulfate.

EXAMPLE 3

A solution of the sodium salt of DAHP obtained by addition of 0.4 mol of cyanoacetic acid metyl ester to 0.8 mol of sodium methylate in methanol and 0.4 mol of guanidine nitrate at the boiling point, followed by removal of the methanol by distillation and addition of water, was converted into a DAHNP suspension by admixing it with 0.4 mol of sodium nitrite and allowing the mixture to flow into 0.44 mol of aqueous 30 wt.-% sulfuric acid. At the beginning the suspension (volume 650 to 700 ml) had a pH of 3.5. It was then admixed with 1.2 g of 5 wt.-% palladized charcoal (corresponding to 60 mg metallic palladium), and the mixture was hydrogenated in a 1 liter lifting autoclave at 90° to 100° C. and 50 bar of hydrogen pressure. After cessation of the hydrogen takeup, the reaction was allowed to continue for another 60 minutes, whereupon the pH of the suspension was 6 to 6.5. Thereafter, the suspension was admixed with 0.44 mol of aqueous sodium hydroxide and, in analogy to Example 1, the catalyst was filtered off, the filtrate was stirred into 0.7 mol aqueous sulfuric acid, and the TAHP-sulfate obtained thereby was filtered off and washed. By means of AAS testing, no palladium could be detected in the TAHP sulfate and in the waste water.

EXAMPLE 4

The procedure described in Example 3 was repeated. Before the beginning of the reaction, the suspension had a pH of 8.5. Immediately after the reaction the pH of the suspension wa 7.5 to 9. By means of AAS testing, no palladium could be detected in the TAHP sulfate and in the waste water.

EXAMPLE 5

A DAHNP suspension obtained in analogy to Example 3 from 8.0 mol of cyanoacetic acid methyl ester, 16.0 mols of sodium methylate, 8.0 mols of guanidine nitrate, 8.0 mols of sodium nitrite and 8.8 mols of sulfuric acid had a pH of 3.5 and a volume of 13 liters. The suspension was hydrogenated at 30 bar and in the presence of 25 g of 5 wt.-% palladized charcoal at 70° to 80° C. in a $V_4A$ propulsion jet loop-type reactor. After the completion of the hydrogen uptake, the mixture was allowed to react for 30 minutes more, whereupon the pH was 6 to 7. The reaction mixture was worked up with 8.8 mols of sodium hydroxide and 14.0 mols of sulfuric acid in analogy to Example 2. AAS-testing did not show any palladium in the TAHP sulfate or in the waste water.

EXAMPLE 6

The procedure described in Example 3 was repeated, but the pH of the suspension prior to the beginning of the reaction was 2.0. Instead of 1.2 g of 5 wt.-% palladized charcoal, 2.5 g of 5 wt.-% pallatinized charcoal were used. Immediately after the reaction, the pH was 6.0. AAS testing did not show any platinum in the TAHP sulfate or in the waste water.

COMPARATIVE EXAMPLE A

The procedure described in Example 3 was repeated, but prior to beginning of the reaction the pH of the suspension was adjusted to 11.0 with dilute sodium hydroxide. Immediately after the reaction, the pH was then 10.2. AAS testing showed that a total of about 20 to 30 mg of palladium were present in the TAHP sulfate and the waste water, which corresponds to 33 to 50% of the noble metal initially used.

COMPARATIVE EXAMPLE B

The procedure described in Example 3 was repeated, but before the beginning of the reaction a pH of 11.3 was adjusted, and instead of 1.2 g of 5 wt.-% palladized charcoal, 2.5 g of 5 wt.-% pallatinized charcoal were used. Immediately after the reaction the pH was 10. AAS testing showed that the waste water contained 55 mg of platinum, which corresponds to 44% of the metallic platinum originally used.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. In the method of preparing 2,4,5-triamino-6-hydroxypyrimidine by catalytic hydrogenation of 2,4-diamino-6-hydroxy-5-nitrosopyrimidine at elevated pressure and elevated temperature in an aqueous medium which may optionally additionally contain organic solvents or inert salts, and in the presence of a noble metal hydrogenation catalyst, the improvement which comprises performing the hydrogenation in an acid, neutral or weakly alkaline range below pH 9, preferably without the addition of alkaline agents prior to and during the hydrogenation, adding the amount of alkaline agent required for dissolution of the 2,4,5-triamino-6-hydroxypyrimidine after the hydrogenation, and separating the catalyst from the solution formed thereby.

2. The method of claim 1, wherein the pH during the hydrogenation is kept below 9.0.

3. The method of claim 2, wherein the pH during the hydrogenation is kept between 3 and 8.5.

4. The method of claim 1, wherein 0.9 to 1.2 mols of sodium hydroxide or potassium hydroxide per mol of 2,4-diamino-6-hydroxy-5-nitrosopyrimidine are used as the base for dissolution of the 2,4,5-triamino-6-hydroxypyrimidine product after completion of the reaction.

5. The method of claim 1, wherein the concentration of 2,4-diamino-6-hydroxy-5-nitrosopyrimidine in the aqueous medium is 0.4 to 3.0 mols/liter.

6. The method of claim 1, wherein the hydrogenation is performed at a hydrogen pressure of 3 to 150 bar.

7. The method of claim 6, wherein the hydrogenation is performed at a hydrogen pressure of 10 to 60 bar.

8. The method of claim 1, wherein the hydrogenation catalyst is ruthenium, palladium, platinum or compounds thereof.

9. The method of claim 1, wherein the hydrogenation catalyst is palladium, palladium oxide, platinum or platinum oxide deposited on activated coal as a carrier material.

10. The method of claim 1, wherein the hydrogenation is performed at temperatures of 50° to 150° C.

11. The method of claim 1, wherein the hydrogenation is performed at temperatures from 70° to 120° C.

12. The method of claim 1, wherein the 2,4-diamino-6-hydroxy-5-nitrosopyrimidine is provided in the form of an aqueous suspension which is obtained from the preparation of this compound starting from guanidine salts, alkali metal alcoholates and cyanoacetic acid esters, followed by nitrosing, without isolation of intermediates and without separation of by-products.

13. The method of claim 1, wherein the separated, used catalyst is again employed as the hydrogenation catalyst in a subsequent reaction batch after addition of 0 to 50% of fresh catalyst thereto.

* * * * *

UNITED STATES PATENT AND TRADEMARK OFFICE
CERTIFICATE OF CORRECTION

PATENT NO. : 5,101,031

DATED : March 31, 1992

INVENTOR(S) : Artur Hunds et al

It is certified that error appears in the above-identified patent and that said Letters Patent is hereby corrected as shown below:

Title Page Inventors, "Walte" should read --Walter--.

Col. 3, line 4, "Jet" should read --jet--.

Col. 5, line 6, "wa" should read --was--.

Signed and Sealed this

Second Day of March, 1993

Attest:

STEPHEN G. KUNIN

Attesting Officer

Acting Commissioner of Patents and Trademarks